(12) United States Patent
Matsushita et al.

(10) Patent No.: US 7,141,693 B2
(45) Date of Patent: Nov. 28, 2006

(54) PROCESS FOR PRODUCING β-OXONITRILE COMPOUND OR ALKALI METAL SALT THEREOF

(75) Inventors: Akio Matsushita, Ube (JP); Kiyotaka Yoshii, Ube (JP); Masayoshi Oue, Ube (JP); Taku Nakamura, Ube (JP); Shuji Yamada, Ube (JP)

(73) Assignee: Ube Industries, Ltd., Ube (JP)

( * ) Notice: Subject to any disclaimer, the term of this patent is extended or adjusted under 35 U.S.C. 154(b) by 100 days.

(21) Appl. No.: 10/485,495

(22) PCT Filed: Aug. 2, 2002

(86) PCT No.: PCT/JP02/07893

§ 371 (c)(1),
(2), (4) Date: Jan. 29, 2004

(87) PCT Pub. No.: WO03/014067

PCT Pub. Date: Feb. 20, 2003

(65) Prior Publication Data

US 2004/0171863 A1    Sep. 2, 2004

(30) Foreign Application Priority Data

Aug. 2, 2001 (JP) .................... 2001-234659

(51) Int. Cl.
*C07C 255/03* (2006.01)
(52) U.S. Cl. ..................................... 558/368
(58) Field of Classification Search ............ 558/368
See application file for complete search history.

(56) References Cited

FOREIGN PATENT DOCUMENTS

| JP | 63-264448 A | 11/1988 |
|---|---|---|
| JP | 2-300155 A | 12/1990 |
| JP | 2000-86637 A | 3/2000 |
| RO | 71248 | 3/1981 |

OTHER PUBLICATIONS

Baldur Fohlisch et al., Synthese Von 3-Oxo-8-oxabicyclo[3.2.1]oct-6-en-2-carbonitrilen aus γ-Bromζ-oxonitrilen-und Furan via [4+3]-cycloaddition von 1-cyanallylium-2-olaten, Chemische Berichte(Chem. Ber.), 115, pp. 355-380, 1982.*
English-language International Preliminary Examination Report dated Jul. 22, 2003 of International Application PCT/JP02/07893 filed Aug. 2, 2002, Applicants: UBE Industries, Ltd.

* cited by examiner

Primary Examiner—Johann Richter
Assistant Examiner—Ebenezer Sackey
(74) Attorney, Agent, or Firm—Frishauf, Holtz, Goodman & Chick, P.C.

(57) ABSTRACT

The present invention relates to a process for preparing a β-oxonitrile compound or an alkali metal salt thereof which comprises reacting a carboxylic ester represented by the formula (1):

$$R^1CO_2R^2 \qquad (1)$$

wherein $R^1$ and $R^2$ each represent a group which does not participate in a reaction, provided that $R^2$ excludes a hydrogen atom, with a nitrile compound represented by the formula (2):

$$R^3CH_2CN \qquad (2)$$

wherein $R^3$ represents an alkyl group, and a base at 145 to 300° C. in a sealed vessel to obtain an alkali metal salt of a β-oxonitrile compound represented by the formula (3):

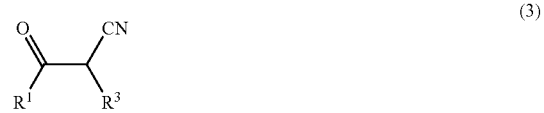

wherein $R^1$ and $R^3$ have the same meanings as defined above,
and neutralizing the same with an acid, if necessary.

20 Claims, No Drawings

PROCESS FOR PRODUCING β-OXONITRILE COMPOUND OR ALKALI METAL SALT THEREOF

This application is the United States national phase application of International Application PCT/JP02/07893 filed Aug. 2, 2002.

TECHNICAL FIELD

The present invention relates to a process for preparing a β-oxonitrile compound or an alkali metal salt thereof useful for synthetic starting materials for medicine, agricultural chemicals, etc.

BACKGROUND ART

As a method for producing a β-oxonitrile derivative or an alkali metal salt thereof by reacting a nitrile compound with a carboxylic ester, there has been disclosed a method, for example, in Romania Patent No. 71248 (RO 71248), in which butyl acetate and propionitrile are reacted in the presence of sodium butoxide in xylene at 125 to 128° C. to obtain an alkali metal salt of α-acetylpropionitrile with a purity of 85 to 87% and a yield of 70 to 75%, and neutralizing and purifying the product to obtain α-acetylpropionitrile with a yield of 50%. Also, in Chemische Berichte (Chem. Ber.), 115, 355 (1982), there is disclosed a method for obtaining 2-methyl-3-oxobutane nitrile by reacting ethyl acetate and propionitrile in the presence of sodium hydride in benzene with a yield of 34%, and further in Journal of American Chemical Society (J. Am. Chem. Soc.), 79, 723 (1957), there is disclosed a method for obtaining 2-methyl-3-oxobutane nitrile by reacting methyl acetate and propionitrile in the presence of sodium amide in liquid ammonia with a yield of 63%.

However, in either of the methods, their yields are low and they are not a method satisfied as an industrial preparation process.

An object of the present invention is to solve the above-mentioned problems and to provide a process for preparing a β-oxonitrile compound or an alkali metal salt thereof which is capable of obtaining a β-oxonitrile compound or an alkali metal salt thereof with a high yield and suitable for industrial preparation process.

SUMMARY OF THE INVENTION

The problems to be solved by the present invention can be solved by a process for preparing an alkali metal salt of a β-oxonitrile compound which comprises reacting a carboxylic ester represented by the formula (1):

$$R^1CO_2R^2 \qquad (1)$$

wherein $R^1$ and $R^2$ each represent a group which does not participate in a reaction, provided that $R^2$ excludes a hydrogen atom, with a nitrile compound represented by the formula (2):

$$R^3CH_2CN \qquad (2)$$

wherein $R^3$ represents an alkyl group, and a base at 145 to 300° C. in a sealed vessel to obtain an alkali metal salt of a β-oxonitrile compound represented by the formula (3):

wherein $R^1$ and $R^3$ have the same meanings as defined above.

BEST MODE FOR CARRYING OUT THE INVENTION

The carboxylic ester to be used in the reaction of the present invention is a compound represented by the above-mentioned formula (1). In the formula (1), $R^1$ is a group which does not participate in the reaction, preferably a hydrogen atom, an alkyl group or an aryl group which may have a substituent(s), and there may be specifically mentioned, for example, a hydrogen atom; a lower alkyl group having 1 to 4 carbon atoms such as a methyl group, an ethyl group, a propyl group, a butyl group, etc.; and an aryl group having 6 to 14 carbon atoms such as a phenyl group, a naphthyl group, an anthryl group, etc. Incidentally, these groups contain various kinds of isomers.

As a substituent(s) for the above-mentioned alkyl group or aryl group, there may be mentioned a lower alkoxy group having 1 to 4 carbon atoms such as a methoxy group, an ethoxy group, a propoxy group, a butoxy group, etc.; and a halogen atom such as a fluorine atom, a chlorine atom, a bromine atom, an iodine atom, etc. Incidentally, a number of the substituent(s) or a position thereof is not specifically limited.

Also, in the formula (1), $R^2$ is a group which does not participate in the reaction except for a hydrogen atom, preferably an alkyl group or an aryl group which may have a substituent(s), specifically, for example, a lower alkyl group having 1 to 4 carbon atoms such as a methyl group, an ethyl group, a propyl group, a butyl group, etc.; and an aryl group having 6 to 14 carbon atoms such as a phenyl group, a naphthyl group, an anthryl group, etc. Incidentally, these groups contain various kinds of isomers.

As a substituent(s) for the above-mentioned alkyl group or aryl group, there may be mentioned a lower alkoxy group having 1 to 4 carbon atoms such as a methoxy group, an ethoxy group, a propoxy group, a butoxy group, etc.; and a halogen atom such as a fluorine atom, a chlorine atom, a bromine atom, an iodine atom, etc. Incidentally, a number of the substituent(s) or a position thereof is not specifically limited.

Specific examples of the carboxylic ester represented by the above-mentioned formula (1), there may be mentioned, for example, formate, acetate, propionate, butyrate, etc.

The nitrile compound to be used in the reaction of the present invention is a compound represented by the above-mentioned formula (2). In the formula (2), $R^3$ is an alkyl group, preferably an alkyl group having 1 to 10 carbon atoms, and there may be specifically mentioned, for example, a methyl group, an ethyl group, a propyl group, a butyl group, a pentyl group, a hexyl group, a heptyl group, an octyl group, a nonyl group, a decyl group, etc. Incidentally, these groups contain various kinds of isomers.

As a specific example of the nitrile compound represented by the above-mentioned formula (2), there may be mentioned, for example, propionitrile, butyronitrile, valeronitrile, hexanenitrile, heptanenitrile, octanenitrile, nonanenitrile, decanenitrile, undecanenitrile, dodecanenitrile (respective compounds include respective isomers).

An amount of the above-mentioned nitrile compound to be used is preferably 0.05 to 20 mol, more preferably 0.1 to 10 mol based on 1 mol of the carboxylic ester.

As the base to be used in the reaction of the present invention, there may be mentioned, for example, an alkali metal alkoxide such as lithium methoxide, sodium methoxide, potassium methoxide, lithium ethoxide, sodium ethoxide, potassium ethoxide, lithium n-butoxide, sodium n-butoxide, potassium n-butoxide, etc.; and a metal hydride such as lithium hydride, sodium hydride, potassium hydride, etc., preferably sodium methoxide, sodium hydride, particularly preferably sodium methoxide is used. Incidentally, these bases may be used singly or in combination of two or more kinds in admixture.

An amount of the above-mentioned base to be used is preferably 0.05 to 10 mol, more preferably 0.1 to 5 mol based on 1 mol of the carboxylic ester.

The reaction of the present invention is carried out in a closed reaction vessel, and a specific example of the reaction vessel to be used may be mentioned, for example, autoclave, etc.

The reaction of the present invention is carried out in the presence or absence of a solvent. The solvent to be used is not specifically limited so long as it does not participate in the reaction, and there may be mentioned, for example, a cyclic aliphatic hydrocarbon such as cyclohexane, cycloheptane, cyclooctane, etc.; a halogenated aliphatic hydrocarbon such as 1,2-dichloroethane, etc.; an aromatic hydrocarbon such as toluene, xylene, cumene, etc.; a halogenated aromatic hydrocarbon such as chlorobenzene, bromobenzene, etc.; a nitrated aromatic hydrocarbon such as nitrobenzene, etc.; an alcohol such as methanol, ethanol, n-propyl alcohol, isopropyl alcohol, n-butyl alcohol, isobutyl alcohol, t-butyl alcohol, etc., preferably a cyclic aliphatic hydrocarbon or an aromatic hydrocarbon is used. Incidentally, these solvents may be used singly or in combination of two or more kinds in admixture.

An amount of the above-mentioned solvent may be optionally controlled depending on uniformity of the solution or stirability of the same, and it is preferably 0 to 100 ml, more preferably 0 to 20 ml based on 1 g of the carboxylic ester.

The reaction of the present invention is carried out by a method in which, for example, in an atmosphere of an inert gas such as nitrogen, argon, etc., a carboxylic ester, a nitrile compound, a base and a solvent are mixed, and the mixture is stirred at 145 to 300° C. in a closed vessel under a spontaneous pressure or a self pressure and the like.

Incidentally, the spontaneous pressure or self pressure in the present invention means a pressure which occurs during the reaction by vaporizing a reaction mixture or a part thereof in a closed reaction vessel, and it is a pressure higher than normal pressure, preferably 0.12 to 10 MPa.

The reaction temperature of the present invention may vary depending on the reaction pressure, and preferably 150 to 200° C.

An alkali metal salt of a β-oxonitrile compound can be obtained by the reaction of the present invention, and it can be obtained by carrying out, for example, concentration, filtration, etc., after completion of the reaction. Also, the alkali metal salt is neutralized in an aqueous solution by adding an inorganic acid such as hydrochloric acid, nitric acid, sulfuric acid, etc., or an organic acid such as acetic acid, benzoic acid, etc., whereby it can be obtained as a free β-oxonitrile compound. Also, these products may be further purified by a conventional method such as recrystallization, distillation, column chromatography, etc.

EXAMPLES

Next, the present invention is specifically mentioned by referring to Examples, but the scope of the present invention is not limited by these.

Example 1

Synthesis of sodium salt of 3-cyano-2-butanone

In an autoclave made of glass having an inner volume of 300 ml and equipped with a stirring device, a thermometer and a pressure gauge were charged 30.2 g (0.26 mol) of n-butyl acetate, 33.1 g (0.60 mol) of propionitrile, 10.8 g (0.20 mol) of sodium methoxide and 83 ml of xylene, and the mixture was reacted at 150° C. under spontaneous pressure (0.29 to 0.32 MPa (gauge pressure)) in a closed reaction vessel for 2 hours under argon atmosphere. After completion of the reaction, the mixture was cooled to room temperature, and precipitated products were collected by filtration and dried to give 20.9 g of a sodium salt of 3-cyano-2-butanone as colorless powder (isolation yield: 87.7%).

Physical property of sodium salt of 3-cyano-2-butanone was as follows.

$^1$H-NMR (DMSO-$d_6$, δ (ppm)); 1.45 (3H, s), 1.75 (3H, s)

Comparative Example 1

Synthesis of sodium salt of 3-cyano-2-butanone

In a flask made of glass having an inner volume of 300 ml and equipped with a stirring device, a thermometer and a reflux condenser were charged 30.2 g (0.26 mol) of n-butyl acetate, 33.1 g (0.60 mol) of propionitrile, 10.8 g (0.20 mol) of sodium methoxide and 83 ml of xylene, and the mixture was reacted under reflux condition (90 to 94° C.) under normal pressure for 24 hours under nitrogen atmosphere. After completion of the reaction, the mixture was cooled to room temperature, and precipitated products were collected by filtration and dried to give 10.1 g of a sodium salt of 3-cyano-2-butanone as colorless powder (isolation yield: 42.4%).

Example 2

Synthesis of 3-cyano-2-butanone

In a flask made of glass having an inner volume of 300 ml were charged 30.0 g (0.25 mol) of sodium salt of 3-cyano-2-butanone synthesized in the same manner as in Example 1, 40 ml of water and 100 ml of ethyl acetate. Then, 21.7 ml (0.26 mol) of conc. hydrochloric acid was gradually added and the organic layer was taken out and dried over anhydrous magnesium sulfate. After filtration, the filtrate was concentrated under reduced pressure to give 23.3 g of 3-cyano-2-butanone (isolation yield: 96.0%).

Physical property of 3-cyano-2-butanone was as follows.

$^1$H-NMR (DMSO-$d_6$, δ (ppm)); 1.50 (3H, s), 2.38 (3H, s), 3.60 (1H, q)

Example 3

Synthesis of sodium salt of 3-cyano-2-butanone

The reaction was carried out in the same manner as in Example 1 except for changing the reaction temperature in Example 1 to 170° C. As a result, 21.9 g of a sodium salt of 3-cyano-2-butanone (isolation yield: 92.0%) was obtained as colorless powder.

Example 4

Synthesis of sodium salt of 3-cyano-2-butanone

The reaction was carried out in the same manner as in Example 1 except for changing the reaction temperature in Example 1 to 200° C. As a result, 20.3 g of a sodium salt of 3-cyano-2-butanone (isolation yield: 85.2%) was obtained as colorless powder.

Example 5

Synthesis of sodium salt of 3-cyano-2-butanone

The reaction was carried out in the same manner as in Example 3 except for changing n-butyl acetate in Example 3 to 22.9 g (0.26 mol) of ethyl acetate. As a result, 21.3 g of a sodium salt of 3-cyano-2-butanone (isolation yield: 89.4%) was obtained as colorless powder.

Example 6

Synthesis of sodium salt of 3-cyano-2-butanone

The reaction was carried out in the same manner as in Example 3 except for changing a used amount of propionitrile in Example 3 to 44.1 g (0.80 mol). As a result, 21.2 g of a sodium salt of 3-cyano-2-butanone (isolation yield: 89.0%) was obtained as colorless powder.

Example 7

Synthesis of sodium salt of 3-cyano-2-butanone

The reaction was carried out in the same manner as in Example 3 except for not using xylene in Example 3. As a result, 18.9 g of a sodium salt of 3-cyano-2-butanone (isolation yield: 79.3%) was obtained as colorless powder.

Example 8

Synthesis of sodium salt of 2-benzoylpropionitrile

In an autoclave made of glass having an inner volume of 100 ml and equipped with a stirring device, a thermometer and a pressure gauge were charged 17.71 g (0.13 mol) of methyl benzoate, 8.27 g (0.15 mol) of propionitrile, 5.41 g (0.10 mol) of sodium methoxide and 40 ml of toluene, and the mixture was reacted at 170° C. under spontaneous pressure (0.49 MPa (gauge pressure)) in a closed reaction vessel for 2 hours under nitrogen atmosphere. After completion of the reaction, the mixture was cooled to room temperature, and precipitated products were collected by filtration and dried to give 15.80 g of sodium salt of 2-benzoylpropionitrile as colorless powder (isolation yield: 87.2%).

Physical property of sodium salt of 2-benzoylpropionitrile was as follows.
$^1$H-NMR (DMSO-$d_6$, δ (ppm)); 1.64 (3H, s), 7.10 to 7.80 (5H, m)

Comparative Example 2

Synthesis of sodium salt of 2-benzoylpropionitrile

In a flask made of glass having an inner volume of 100 ml and equipped with a stirring device, a thermometer and a reflux condenser were charged 17.71 g (0.13 mol) of methyl benzoate, 8.27 g (0.15 mol) of propionitrile, 5.41 g (0.10 mol) of sodium methoxide and 40 ml of toluene, and the mixture was reacted under nitrogen atmosphere and reflux condition (90 to 94° C.) at normal pressure for 24 hours. After completion of the reaction, the mixture was cooled to room temperature, and precipitated products were collected by filtration and dried to give 12.80 g of a sodium salt of 2-benzoylpropionitrile (isolation yield: 70.6%) as colorless powder.

Example 9

Synthesis of sodium salt of 2-formylpropionitrile

In an autoclave made of glass having an inner volume of 100 ml and equipped with a stirring device, a thermometer and a pressure gauge were charged 9.63 g (0.13 mol) of ethyl formate, 8.27 g (0.15 mol) of propionitrile, 5.41 g (0.10 mol) of sodium methoxide and 40 ml of toluene, and the mixture was reacted at 170° C. under spontaneous pressure (0.22 MPa (gauge pressure)) in a closed reaction vessel for 2 hours under nitrogen atmosphere. After completion of the reaction, the mixture was cooled to room temperature, and precipitated products were collected by filtration and dried to give 7.35 g of a sodium salt of 2-formylpropionitrile (isolation yield: 70.0%) as colorless powder.

Physical property of sodium salt of 2-formylpropionitrile was as follows.
$^1$H-NMR (DMSO-$d_6$, δ (ppm)); 1.42 (3H, s), 8.12 (1H, s)

Comparative Example 3

Synthesis of sodium salt of 2-formylpropionitrile

In a flask made of glass having an inner volume of 200 ml and equipped with a stirring device, a thermometer and a reflux condenser were charged 9.63 g (0.13 mol) of ethyl formate, 8.27 g (0.15 mol) of propionitrile, 5.41 g (0.10 mol) of sodium methoxide and 40 ml of toluene, and the mixture was reacted under nitrogen atmosphere at normal pressure at 90° C. for 24 hours. After completion of the reaction, the mixture was cooled to room temperature, and precipitated products were collected by filtration and dried to give 2.90 g of colorless powder. This powder was analyzed by $^1$H-NMR (DMSO-$d_6$), and no sodium salt of 2-formylpropionitrile was formed.

Example 10

Synthesis of sodium salt of 3-cyano-2-pentanone

In an autoclave made of glass having an inner volume of 300 ml and equipped with a stirring device, a thermometer and a pressure gauge were charged 30.2 g (0.26 mol) of n-butyl acetate, 41.7 g (0.60 mol) of butyronitrile, 10.8 g (0.20 mol) of sodium methoxide and 83 ml of xylene, and the mixture was reacted at 150° C. under spontaneous pressure (0.29 MPa (gauge pressure)) in a closed reaction vessel for 2 hours under nitrogen atmosphere. After completion of the reaction, the mixture was cooled to room temperature, and precipitated products were collected by filtration and dried to give 23.4 g of a sodium salt of 3-cyano-2-pentanone (isolation yield: 87.9%) as colorless powder.

Physical property of sodium salt of 3-cyano-2-pentanone was as follows.

$^1$H-NMR (DMSO-$d_6$, δ (ppm)); 0.83 (3H, t), 1.73 (3H, s), 1.92 (2H, q)

Example 11

Synthesis of 3-cyano-2-pentanone

In a flask made of glass having an inner volume of 300 ml were charged 33.3 g (0.25 mol) of a sodium salt of 3-cyano-2-pentanone synthesized in the same manner as in Example 10, 40 ml of water and 100 ml of ethyl acetate. Then, 21.7 ml (0.26 mol) of conc. hydrochloric acid was gradually added to the mixture, and the organic layer was taken out and dried over anhydrous magnesium sulfate. After filtration, the filtrate was concentrated under reduced pressure to give 26.4 g of 3-cyano-2-pentanone (isolation yield: 95.0%) as colorless liquid.

Physical property of 3-cyano-2-pentanone was as follows.
$^1$H-NMR (DMSO-$d_6$, δ (ppm)); 0.97 (3H, t), 1.95 to 2.22 (2H, m), 2.26 (3H, s), 4.02 to 4.12 (1H, m)

UTILIZABILITY IN INDUSTRY

According to the present invention, a β-oxonitrile compound or an alkali metal salt thereof can be obtained with a high yield, and a process for preparing a β-oxonitrile compound or an alkali metal salt thereof which is industrially suitable can be provided.

The invention claimed is:

1. A process for preparing an alkali metal salt of a β-oxonitrile compound which comprises reacting a carboxylic ester represented by the formula (1):

$R^1CO_2R^2$     (1)

wherein $R^1$ and $R^2$ each represent a group which does not participate in a reaction, provided that $R^2$ excludes a hydrogen atom, with a nitrile compound represented by the formula (2):

$R^3CH_2CN$     (2)

wherein $R^3$ represents an alkyl group, and a base at 145 to 300° C. in a sealed vessel to obtain an alkali metal salt of a β-oxonitrile compound represented by the formula (3):

(3)

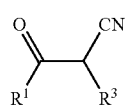

wherein $R^1$ and $R^3$ have the same meanings as defined above.

2. The process for preparing an alkali metal salt of a β-oxonitrile compound according to claim 1, wherein a pressure at the time of the reaction is 0.12 to 10 MPa.

3. The process for preparing an alkali metal salt of a β-oxonitrile1e compound according to claim 1, wherein the nitrile compound is used in an amount of 0.05 to 20 mol based on 1 mol of the carboxylic ester.

4. The process for preparing an alkali metal salt of a β-oxonitrile compound according to claim 1, wherein the nitrile compound is used in an amount of 0.1 to 10 mol based on 1 mol of the carboxylic ester.

5. The process for preparing an alkali metal salt of a β-oxonitrile compound according to claim 1, wherein the base is selected from the group consisting of an alkali metal alkoxide and a metal hydride.

6. The process for preparing an alkali metal salt of a β-oxonitrile compound according to claim 1, wherein the base is selected from the group consisting of lithium methoxide, sodium methoxide, potassium methoxide, lithium ethoxide, sodium ethoxide, potassium ethoxide, lithium n-butoxide, sodium n-butoxide, potassium n-butoxide, lithium hydride, sodium hydride and potassium hydride.

7. The process for preparing an alkali metal salt of a β-oxonitrile compound according to claim 1, wherein the base is sodium methoxide or sodium hydride.

8. The process for preparing an alkali metal salt of a β-oxonitrile compound according to claim 1, wherein the base is sodium methoxide.

9. The process for preparing an alkali metal salt of a β-oxonitrile compound according to claim 1, wherein the base is used in an amount of 0.05 to 10 mol based on 1 mol of the carboxylic ester.

10. The process for preparing an alkali metal salt of a β-oxonitrile compound according to claim 1, wherein the base is used in an amount of 0.1 to 5 mol based on 1 mol of the carboxylic ester.

11. The process for preparing an alkali metal salt of a β-oxonitrile compound according to claim 1, wherein the reaction is carried out in the presence or absence of a solvent.

12. The process for preparing an alkali metal salt of a β-oxonitrile compound according to claim 1, wherein the reaction is carried out in the presence of a solvent selected from the group consisting of a cyclic aliphatic hydrocarbon, a halogenated aliphatic hydrocarbon, an aromatic hydrocarbon, a halogenated aromatic hydrocarbon, a nitrated aromatic hydrocarbon and an alcohol.

13. The process for preparing an alkali metal salt of a β-oxonitrile compound according to claim 1, wherein the reaction is carried out in the presence of a solvent selected from the group consisting of cyclohexane, cycloheptane, cyclooctane, 1,2-dichloroethane, toluene, xylene, cumene, chlorobenzene, bromobenzene, nitrobenzene, methanol, ethanol, n-propyl alcohol, isopropyl alcohol, n-butyl alcohol, isobutyl alcohol and t-butyl alcohol.

14. The process for preparing an alkali metal salt of a β-oxonitrile compound according to claim 1, wherein the process is carried out in the presence of a solvent, and the solvent is used in an amount of 0 to 100 ml based on 1 g of the carboxylic ester.

15. The process for preparing an alkali metal salt of a β-oxonitrile compound according to claim 1, wherein the process is carried out in the presence of a solvent, and the solvent is used in an amount of 0 to 20 ml based on 1 g of the carboxylic ester.

16. A process for preparing a β-oxonitrile compound which comprises neutralizing an alkali metal salt of the β-oxonitrile compound prepared by the process as defined in claim 1 with an acid.

17. The process for preparing a β-oxonitrile compound according to claim 16, wherein the acid is selected from the group consisting of hydrochloric acid, nitric acid and sulfuric acid.

18. The process for preparing a β-oxonitrile compound according to claim 1, wherein the carboxylic ester is selected from the group consisting of formate, acetate, propionate and butyrate.

19. The process for preparing a β-oxonitrile compound according to claim 18, wherein the nitrile compound is selected from the group consisting of propionitrile, butyronitrile, valeronitrile, hexanenitrile, heptanenitrile, octanenitrile, nonanenitrile, decanenitrile, undecanenitrile and dodecanenitrile.

20. The process for preparing a β-oxonitrile compound according to claim 1, wherein the β-oxonitrile compound is selected from the group consisting of 3-cyano-2-butanone, 2-benzoylpropionitrile, 2formylpropionitrile and 3-cyano2-pentanone.

* * * * *